United States Patent
Kuramoto et al.

(10) Patent No.: US 9,243,075 B2
(45) Date of Patent: Jan. 26, 2016

(54) N-ACYLAMINO ACID DERIVATIVES OF CELLULOSE OR STARCH BASED POLYSACCHARIDES AND EMULSIFIED PRODUCTS CONTAINING THE SAME

(75) Inventors: Masayuki Kuramoto, Kanagawa (JP); Tatsuya Hattori, Kanagawa (JP); Masahiro Ino, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 55 days.

(21) Appl. No.: 13/599,650

(22) Filed: Aug. 30, 2012

(65) Prior Publication Data

US 2013/0231402 A1    Sep. 5, 2013

(30) Foreign Application Priority Data

Aug. 30, 2011 (JP) ................................ 2011-187405

(51) Int. Cl.
| | |
|---|---|
| C08B 31/02 | (2006.01) |
| C08B 15/06 | (2006.01) |
| C08L 3/06 | (2006.01) |
| C08B 31/04 | (2006.01) |
| C08B 15/00 | (2006.01) |
| C08B 31/00 | (2006.01) |
| C08L 1/08 | (2006.01) |
| A61K 8/06 | (2006.01) |
| A61Q 19/00 | (2006.01) |
| A61K 8/73 | (2006.01) |
| C08B 11/02 | (2006.01) |
| C08B 11/08 | (2006.01) |
| C08L 3/04 | (2006.01) |

(52) U.S. Cl.
CPC ................ *C08B 31/02* (2013.01); *A61K 8/062* (2013.01); *A61K 8/731* (2013.01); *A61K 8/732* (2013.01); *A61Q 19/00* (2013.01); *C08B 15/00* (2013.01); *C08B 15/06* (2013.01); *C08B 31/00* (2013.01); *C08B 31/04* (2013.01); *C08L 1/08* (2013.01); *C08L 3/06* (2013.01); *A61K 2800/10* (2013.01); *C08B 11/02* (2013.01); *C08B 11/08* (2013.01); *C08L 3/04* (2013.01)

(58) Field of Classification Search
None
See application file for complete search history.

(56) References Cited

U.S. PATENT DOCUMENTS

| | | | | |
|---|---|---|---|---|
| 2,808,405 | A * | 10/1957 | Novak et al. | ..... 536/51 |
| 6,248,338 | B1 | 6/2001 | Muller et al. | |
| 2005/0265951 | A1 * | 12/2005 | Yamawaki et al. | ..... 424/70.22 |

FOREIGN PATENT DOCUMENTS

JP    2010-106068    5/2010

OTHER PUBLICATIONS

Seki, T., Aoi, K., Okada, M., & Shiogai, Y. (2000). Synthesis of chitin derivatives having peptide side groups by the water-soluble active ester method. Macromolecular Chemistry and Physics, 201(4), 439-446.*
Kochetkov, N. K., Khachatur'yan, A. A., Vasil'ev, A. E., & Rozenberg, G. Y. (1969). Dextran derivatives I. Synthesis of O-aminoacyl derivatives of dextran. Chemistry of Natural Compounds, 5(5), 354-356.*
Wales, M., Marshall, P. A., & Weissberg, S. G. (1953). Intrinsic viscosity—molecular weight relationships for dextran. Journal of Polymer Science, 10(2), 229-240.*

* cited by examiner

*Primary Examiner* — Shaojia Anna Jiang
*Assistant Examiner* — Dale R Miller
(74) *Attorney, Agent, or Firm* — Oblon, McClelland, Maier & Neustadt, L.L.P.

(57) ABSTRACT

To provide a novel substance having an excellent water-dispersibility capable of forming an emulsion which spreads rapidly onto the skin, does not undergo aggregation or segregation due to a salt, and is excellent in a low temperature stability. The aforementioned problems were found to be solved by means of a certain polysaccharide and the invention was established.

13 Claims, No Drawings

N-ACYLAMINO ACID DERIVATIVES OF CELLULOSE OR STARCH BASED POLYSACCHARIDES AND EMULSIFIED PRODUCTS CONTAINING THE SAME

CROSS REFERENCES TO RELATED APPLICATIONS

This application claims priority to Japanese Patent Application No. 187405/2011, filed on Aug. 30, 2011, which is incorporated herein by reference in its entirety.

BACKGROUND OF THE INVENTION

1. Field of the Invention

The present invention relates to polysaccharides and an emulsified products containing the same.

2. Discussion of the Background

An emulsion is employed widely in an industrial field as a form capable of dispersing a water-insoluble substance into water and an oil-insoluble substance into oil. Typically, it is employed in various products including cosmetics, pharmaceuticals, agrochemicals, adhesives, resins, paints and the like.

Since an emulsified condition is unstable thermodynamically, and subjected to various attempts to keep it over a prolonged period. For example, a stabilization by thickening the system is conducted generally. One example of the techniques for thickening is to add a water-soluble polymer such as a carboxyvinyl polymer. However, the stabilization of the emulsion by the thickening has a drawback experienced as a substantial change in the touch of the emulsion, which is characterized typically by a slower spreadability onto the skin. In addition, some types of the water-soluble polymers are less resistant to salts, and in that case, the emulsion may undergo segregation or aggregation without showing a stability of the emulsified condition in the presence of salts. Because of this, the some types of the water-soluble polymers sometimes can not be used together with inorganic salts, plant extracts and sea water extracts as well as vitamins.

In Patent Literature 1, a starch and a hydroxyalkyl starch are employed to achieve a stable emulsified condition. However, the hydroxyalkyl starch is poorly dispersed in water, and may cause precipitation. In addition, the stability of the emulsification at a low temperature still involves problems.

On the other hand, Patent Literature 2 describes that a gel composition containing a certain acyl group-containing composition is preferably stable. However the acyl group-containing composition thickens an aqueous component into a gel, thereby it still has a problem with regard to the spreadability onto the skin. In addition, the stability of the emulsification at an acidic condition remains unsolved.

[Patent Literature 1] JP-T-2000-514435 (the term "JP-T" as used herein means a published Japanese translation of a PCT present application)

[Patent Literature 2] Domestic Re-publication of PCT patent application WO2004-20394

SUMMARY OF THE INVENTION

The problem to be solved by the invention is to provide a novel substance having an excellent water-dispersibility capable of forming an emulsion which spreads rapidly onto the skin, does not undergo aggregation or segregation due to a salt, and is excellent in a low temperature stability.

Means For Solving The Problems

As a result of an intensive study to solve the aforementioned problems, the present invention was established by a certain polysaccharides. Thus the present invention includes the following embodiments.

[1] A polysaccharide represented by Formula (1):

in which A represents a polysaccharide residue, R represents an acyl group derived from a saturated or unsaturated fatty acid having 1 to 22 carbon atoms, —CO—X—NH— represents an amino acid residue, and n represents 50 to 20,000, wherein a weight average molecular weight of the polysaccharide is 1,100,000 to 10,000,000.

[2] The polysaccharide according to [1] wherein the amino acid is one or more selected from the group consisting of aspartic acid, alanine, arginine, ornithine, glycine, glutamic acid, threonine, serine and lysine.

[3] The polysaccharide according to [1] or [2] wherein R is an acyl group derived from a saturated or unsaturated fatty acid having 8 to 22 carbon atoms.

[4] The polysaccharide according to any one of [1] to [3] wherein A represents one or more selected from the group consisting of cellulose residue, starch residue, hydroxyethylcellulose residue, methylcellulose residue, ethylcellulose residue, and hydroxypropylcellulose residue.

[5] The polysaccharide according to any one of [1] to [4] wherein the degree of dispersion of the polysaccharide is 1.2 to 100.

[6] An emulsified product comprising a polysaccharide according to any one of [1] to [5].

[7] The emulsified product according to [6] wherein the polysaccharide content is 0.001% by weight to 5% by weight.

[8] A method for producing a polysaccharide comprising reacting an N-acylamino acid, salt thereof, anhydride thereof, or ester thereof with a precursor polysaccharide or a precursor modified polysaccharide.

By means of a polysaccharide having an excellent water-dispersibility, we can provide an emulsified product which spreads rapidly onto the skin, does not undergo aggregation or segregation due to a salt, and is excellent in a low temperature stability.

DETAILED DESCRIPTION OF THE PREFERRED EMBODIMENTS

Polysaccharide.

The polysaccharide of the present invention is represented by Formula (1). Any salt thereof, for example a salt form of the amino acid residue is also included in the scope of the claimed invention.

In Formula (1), A represents a polysaccharide residue. As used herein, the polysaccharide residue means "a residue derived from a polysaccharide or a modified polysaccharide having a hydroxy group and/or an amino group, which is a remainder resulting from deletion of a hydrogen atom from the hydroxy group and/or the amino group". A is bound to —CO—X—NH—R groups, the number of which is n, via the hydroxy group and/or the amino group whose hydrogen atom was deleted as mentioned above (i.e., —O—, —NH—). The polysaccharide for the polysaccharide residue is not limited particularly as long as it is a polysaccharide or a modified polysaccharide, and is preferably a polysaccharide undergoing Molisch reaction. As used herein, the Molisch reaction is "a reddish purple color exhibiting reaction upon addition of sulfuric acid and 1-naphthol", which is one of the testing methods for detecting polysaccharides. Typically, the polysaccharide for the polysaccharide residue according to the present invention may be a polysaccharide such as cellulose, guar gum, starch, pullulan, dextran, fructan, inulin, mannan, agar, carageenan, chitin, chitosan, pectin, alginic acid and hyaluronic acid and the like; a modified polysaccharide such as hydroxyethylcellulose, hydroxyethylethylcellulose, hydroxyethyl guar gum, hydroxyethyl starch, methylcellulose, methyl guar gum, methyl starch, ethylcellulose, ethyl guar gum, ethyl starch, hydroxypropylcellulose, hydroxypropyl guar gum, hydroxypropyl starch, hydroxyethylmethylcellulose, hydroxyethylmethyl guar gum, hydroxyethylmethyl starch, hydroxypropylmethylcellulose, hydroxypropylmethyl guar gum, hydroxypropylmethyl starch and the like. Among these, cellulose, starch, hydroxyethylcellulose, methylcellulose, ethylcellulose and hydroxypropylcellulose are preferred because of a reduced coloration upon reaction. Cellulose, starch, hydroxyethylcellulose and hydroxypropylcellulose are more preferred and starch is further preferred.

The starch is a mixture of amylose having a high linearity and a relatively low molecular weight and an amylopectin having a low linearity and a relatively high molecular weight. It is generally known that these amylose and amylopectin contents differ depending on the origin of the starch. Since the amylopectin having a low linearity and a large number of branched structures leads to thickening, a starch having an amylopectin content of 85% by weight or less is preferable for the purpose of keeping a low viscosity. On the other hand, a low amylopectin content leads to an elevated gelatinization temperature, resulting in a poor water-dispersibility. In order to ensuring the water-dispersibility, a starch whose amylopectin content is 70% or more is preferred. More preferably, a starch having an amylopectin content of 72% by weight to 78% by weight is employed. From such a point of view, corn starch, tapioca starch, wheat starch, rice starch, potato starch, sweet potato starch are preferred, and corn starch is more preferred.

In Formula (1), R represents an acyl group derived from a straight-chained or branched-chained, saturated or unsaturated fatty acid having 1 to 22 carbon atoms. Typically, octanoyl group, decanoyl group, lauroyl group, myristoyl group, palmitoyl group, stearoyl group, behenyl group, oleoyl group or cocoyl group may be exemplified. An acyl group of a straight-chained or branched-chained, saturated or unsaturated fatty acid having 8 to 22 carbon atoms is preferred. Lauroyl group, myristoyl group, palmitoyl group, stearoyl group, cocoyl group are more preferred, and lauroyl group, cocoyl group are further preferred, and lauroyl group is especially preferred.

In Formula (1), —CO—X—NH— represents an amino acid residue. The amino acid is not limited particularly, as long as it is an amino acid, and typically glycine, alanine, valine, leucine, isoleucine, proline, methionine, cystaine, serine, threonine, asparagine, glutamine, phenylalanine, tyrosine, tryptophan, aspartic acid, glutamic acid, lysine, arginine, histidine, γ-aminobutyric acid and ornithine may be exemplified. Those preferred are aspartic acid, alanine, arginine, ornithine, glycine, glutamic acid, threonine, serine, and lysine. Aspartic acid and glutamic acid are more preferred, and glutamic acid is further preferred. Any salt thereof, for example a salt form of the amino acid residue is also included in the scope of the claimed invention.

When the —CO—X—NH— is aspartic acid or glutamic acid residue, X can have a structure of Formula (2) or Formula (3).

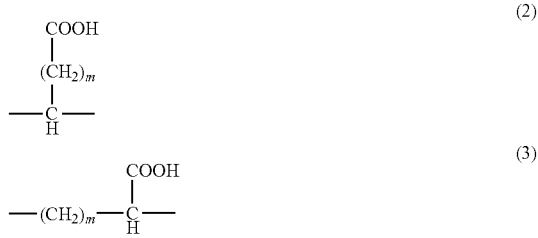

In Formula (2) and Formula (3), m is 1, When the —CO—X—NH— is aspartic acid residue; and m is 2, When the —CO—X—NH— is glutamic acid residue.

The amino acid may form a salt. The salt is not limited particularly, and typically a basic salt including an alkaline metal salt such as sodium salt and potassium salt, an alkaline earth metal salt such as magnesium salt and calcium salt, an inorganic salt such as ammonium salt, an organic amine salt such as monoethanolamine salt, diethanolamine salt, triethanolamine salt, 2-amino-2-methyl-1-propanol salt, 2-amino-2-methyl-1,3-propanediol salt, lysine salt, ornithine salt, arginine salt, and the like; an acidic salt such as an inorganic acid salt such as hydrochloric acid salt, sulfuric acid salt, carbonic acid salt, phosphoric acid salt, an organic acid salt such as acetic acid salt, tartaric acid salt, citric acid salt, p-toluenesulfonic acid salt, glycolic acid salt, malic acid salt, lactic acid salt, fatty acid salt, acidic amino acid salt, pyroglutamic acid salt, and the like. Any of these may be employed alone or in combination of two or more.

In Formula (1), n is an index showing the number of —CO—X—NH—R groups introduced in the polysaccharide. The n also serves as an index representing a % reaction. The n is a mean value of all molecules of the polysaccharide represented by Formula (1) contained in the polysaccharide of this invention. This value is preferably 50 to 20,000. For obtaining a stable emulsion undergoing no aggregation or segregation due to a salt, the lower limit value is preferably 100 or more, more preferably 300 or more, and especially 500 or more. For the purpose of obtaining a product capable of achieving satisfactory viscosity and water-dispersibility The upper limit value is preferably 10000 or less, more preferably 5000 or less, and especially 3000 or less.

The polysaccharide according to the invention is a polysaccharide derivative represented by Formula (1). A polymer composition contains molecules which vary widely. The molecular weight of a polymer composition is represented generally as a weight average molecular weight. As used herein, the "weight average molecular weight" means a weight average molecular weight calculated in terms of dextran measured by a gel permeation chromatography (GPC). For the purpose of achieving sufficient emulsification stability, the weight average molecular weight of the polysaccharide of the present invention is preferably 1,100,000 or more, more preferably 1,300,000 or more, further preferably 1,500,000 or more, and especially 1,700,000 or more. Taking a reduction in the affinity with water into account, the upper limit is preferably 10,000,000 or less, more preferably 9,000,000 or less, especially 8,000,000 or less.

The polysaccharide of the present invention has a molecular weight distribution, which can be represented as a degree of dispersion. The degree of dispersion can be calculated as a value of the weight average molecular weight divided by the number average molecular weight, wherein the weight average molecular weight and the number average molecular weight can be determined by a gel permeation chromatography (GPC) measurement. A higher degree of dispersion means a wider molecular weight distribution. In view of the excellence in the touch, the degree of dispersion of the polysaccharide of the present invention is preferably 1.1 or more, more preferably 1.2 or more, especially 1.3 or more. In view of the tendency that an excessively high degree of dispersion results in a difficulty in production, the degree of dispersion of the polysaccharide of the present invention is preferably 100 or less, more preferably 80 or less, especially 50 or less.

Methods for Producing Polysaccharide.

The polysaccharide of the present invention can be prepared by reacting an N-acylamino acid, salt thereof, anhydride thereof or ester thereof with a precursor polysaccharide or precursor modified polysaccharide.

Reaction of N-Acylamino Acid or Salt Thereof with Precursor Polysaccharide or Precursor Modified Polysaccharide.

The polysaccharide of the present invention can be prepared by subjecting an N-acylamino acid or salt thereof and a precursor polysaccharide or precursor modified polysaccharide to a heating reaction in a reaction solvent in the presence of a condensing agent and a reaction catalyst.

The amino acid of the N-acylamino acid is not limited particularly as long as it is an amino acid, and typically glycine, alanine, valine, leucine, isoleucine, proline, methionine, cystaine, serine, threonine, asparagine, glutamine, phenylalanine, tyrosine, tryptophan, aspartic acid, glutamic acid, lysine, arginine, histidine, γ-aminobutyric acid and ornithine may be exemplified. Aspartic acid, alanine, arginine, ornithine, glycine, glutamic acid, threonine, serine, and lysine are preferred. Aspartic acid and glutamic acid are more preferred, and glutamic acid is especially preferred. The N-acylamino acid may be an optically-active form or a racemic form.

The salt of the N-acylamino acid is not limited, and typically, a basic salt including an alkaline metal salt such as sodium salt and potassium salt, an alkaline earth metal salt such as magnesium salt and calcium salt, an inorganic salt such as ammonium salt, an organic amine salt such as monoethanolamine salt, diethanolamine salt, triethanolamine salt, 2-amino-2-methyl-1-propanol salt, 2-amino-2-methyl-1,3-propanediol salt, lysine salt, ornithine salt, arginine salt, and the like; an acidic salt such as an inorganic acid salt such as hydrochloric acid salt, sulfuric acid salt, carbonic acid salt, phosphoric acid salt, an organic acid salt such as acetic acid salt, tartaric acid salt, citric acid salt, p-toluenesulfonic acid salt, glycolic acid salt, malic acid salt, lactic acid salt, fatty acid salt, acidic amino acid salt, pyroglutamic acid salt, and the like. Any of these may be employed alone or in combination of two or more.

The acyl group of an N-acylamino acid is an acyl group of a straight-chained or branched-chained, saturated or unsaturated fatty acid having 1 to 22 carbon atoms. Examples are octanoyl group, decanoyl group, lauroyl group, myristoyl group, palmitoyl group, stearoyl group, behenyl group, oleyl group or cocoyl group. An acyl group of a straight-chained or branched-chained, saturated or unsaturated fatty acid having 8 to 22 carbon atoms is preferred. Those more preferred are lauroyl group, myristoyl group, palmitoyl group, stearoyl group or cocoyl group, those further preferred are lauroyl group, cocoyl group. Lauroyl group is especially preferred. The acyl group may be bound to an amino group in its α-position, or may be bound to an amino group in a position other than the α-position.

The N-acylamino acid or salt thereof may be prepared by a known method, and can readily be obtained for example by reacting an amino acid or salt thereof with an acyl halide. It is also possible to use a commercially available product. Those which can be exemplified are "Amisoft" LA-D(Nα-lauroyl-L-glutamic acid, manufactured by Ajinomoto Co., Inc.), "Amisoft" CA(Nα-cocoyl-L-glutamic acid, manufactured by Ajinomoto Co., Inc.), "Amisoft" HA-P(Nα-stearoyl-L-glutamic acid, manufactured by Ajinomoto Co., Inc.), "Amihope LL" (Nε-lauroyl-L-lysine, manufactured by Ajinomoto Co., Inc.).

The precursor polysaccharide or precursor modified polysaccharide is a compound resulting from a polymerization of a large number of monosaccharide molecules combined via a glycoside bond. The precursor polysaccharide may be cellulose, guar gum, starch, pullulan, dextran, fructan, inulin, mannan, agar, carageenan, chitin, chitosan, pectin, alginic acid and hyaluronic acid and the like. The precursor modified polysaccharide may be hydroxyethylcellulose, hydroxyethylethylcellulose, hydroxyethyl guar gum, hydroxyethyl starch, methylcellulose, methyl guar gum, methyl starch, ethylcellulose, ethyl guar gum, ethyl starch, hydroxypropylcellulose, hydroxypropyl guar gum, hydroxypropyl starch, hydroxyethylmethylcellulose, hydroxyethylmethyl guar gum, hydroxyethylmethyl starch, hydroxypropylmethylcellulose, hydroxypropylmethyl guar gum, hydroxypropylmethyl starch. Because of reduced coloration, cellulose, starch, hydroxyethylcellulose, methylcellulose, ethylcellulose, and hydroxypropylcellulose are preferred. Cellulose, starch, hydroxyethylcellulose, and hydroxypropylcellulose are more preferred, and starch is especially preferred.

The starch is a mixture of amylose having a high linearity and a relatively low molecular weight and an amylopectin having a low linearity and a relatively high molecular weight. It is generally known that these amylose and amylopectin contents differ depending on the origin of the starch. Since the amylopectin having a low linearity and a large number of branched structures leads to thickening, a starch having an amylopectin content of 85% by weight or less is preferable for the purpose of keeping a low viscosity. On the other hand, a low amylopectin content leads to an elevated gelatinization temperature, resulting in a poor water-dispersibility. In order to ensuring the water-dispersibility, a starch whose amylopectin content is 70% or more is preferred. More preferably, a starch having an amylopectin content of 72% by weight to 78% by weight is employed. From such a point of view, corn starch, tapioca starch, wheat starch, rice starch, potato starch, sweet potato starch are preferred, and corn starch is more preferred.

As a condensing agent, 1-ethyl-3-(3-dimethylaminopropyl)carbodiimide hydrochloride, dicyclohexylcarbodiimide and diisopropylcarbodiimide may be exemplified.

As a reaction catalyst, N,N-4-dimethylaminopyridine, 1-hydroxybenzotriazole and N-hydroxysuccinimide may be exemplified.

As a reaction solvent, dimethylsulfoxide (DMSO), dichloromethane, chloroform, dimethylformamide (DMF), toluene, xylene, ethyl acetate, n-hexane, isopropyl alcohol, 2-methyl-2-isopropyl alcohol and acetone may be exemplified.

The reaction temperature is 50° C. to 150° C., preferably 60° C. to 100° C., more preferably 65 to 75° C.

The reaction temperature is 1 to 24 hours, preferably 3 to 8 hours, more preferably 5 hours.

The concentration of the N-acylamino acid or salt thereof before starting the reaction is adjusted to 0.1 to 25% by weight, preferably 0.5 to 15% by weight, more preferably 1 to 10% by weight.

The concentration of the precursor polysaccharide or precursor modified polysaccharide before starting the reaction is adjusted to 1 to 50% by weight, preferably 3 to 25% by weight, more preferably 5 to 15% by weight.

The concentration of the condensing agent before starting the reaction is adjusted to 0.2 to 35% by weight, preferably 0.7 to 25% by weight, more preferably 1 to 15% by weight.

While the molar ratio of the N-acylamino acid or salt thereof and the precursor polysaccharide or precursor modified polysaccharide employed in the reaction (N-acylamino acid or salt thereof: precursor polysaccharide or precursor modified polysaccharide) is not limited particularly as long as the reaction can be effected, it is preferably 50:1 to 20000:1. In view of an ability of providing a product having a stable emulsification performance without undergoing aggregation or segregation due to a salt, the ratio is preferably 100:1 to 20000:1, more preferably 200:1 to 20000:1, further preferably 300:1 to 20000:1, particularly 400:1 to 20000:1, and especially 500:1 to 20000:1. In view of an ability of providing a product capable of achieving satisfactory viscosity and water-dispersibility, the ratio is preferably 50:1 to 10000:1, more preferably 50:1 to 5000:1, further preferably 50:1 to 3000:1, particularly 50:1 to 2500:1.

Reaction of N-Acylamino Acid Anhydride and Precursor Polysaccharide or Precursor Modified Polysaccharide.

By subjecting an N-acylamino acid anhydride and a precursor polysaccharide or precursor modified polysaccharide to a heating reaction in a reaction solvent, a polysaccharide of the present invention can be prepared.

The N-acylamino acid anhydride can be used as a reaction substrate only when the amino acid is an acidic amino acid. The acidic amino acid may be aspartic acid and glutamic acid. Glutamic acid is preferred in view of a satisfactory progression of the reaction.

The N-acylamino acid anhydride may be prepared using a known method, and can readily be obtained for example by reacting an N-acylamino acid or salt thereof with an acetic anhydride. A commercially available product may also be employed.

The acyl group, precursor polysaccharide or precursor modified polysaccharide, reaction solvent, reaction temperature, reaction time and concentration before starting the reaction to be employed in the reaction can be those described for the reaction of an N-acylamino acid or salt thereof.

While the molar ratio of the N-acylamino acid anhydride and the precursor polysaccharide or precursor modified polysaccharide employed in the reaction (N-acylamino acid anhydride: precursor polysaccharide or precursor modified polysaccharide) is not limited particularly as long as the reaction can be effected, it is preferably 50:1 to 20000:1. In view of an ability of obtaining a product having a stable emulsification performance without undergoing aggregation or segregation due to a salt, the ratio is preferably 100:1 to 20000:1, more preferably 200:1 to 20000:1, further preferably 300:1 to 20000:1, particularly 400:1 to 20000:1, and especially 500:1 to 20000:1. In view of an ability of providing a product capable of achieving satisfactory viscosity and water-dispersibility, the ratio is preferably 50:1 to 10000:1, more preferably 50:1 to 5000:1, further preferably 50:1 to 3000:1, particularly 50:1 to 2500:1.

Reaction of N-Acylamino Acid Ester and Precursor Polysaccharide or Precursor Modified Polysaccharide.

By subjecting an N-acylamino acid ester and a precursor polysaccharide or precursor modified polysaccharide to a heating reaction in a reaction solvent, a polysaccharide of the present invention can be prepared.

The ester in an N-acylamino acid ester is preferably $C_{1-6}$ alkyl ester, more preferably methyl ester, ethyl ester, propyl ester, isopropyl ester, butyl ester, t-butyl ester, pentyl ester, hexyl ester, further preferably methyl ester, ethyl ester.

The N-acylamino acid ester may be prepared by using a known method, and can readily be obtained for example by reacting an N-acylamino acid or salt thereof with a $C_{1-6}$ alkyl alcohol in any of alcoholic solvents in the presence of hydrochloric acid or sulfuric acid. A commercially available product may also be employed.

The acyl group, precursor polysaccharide or precursor modified polysaccharide, reaction solvent, reaction temperature, reaction time and concentration before starting the reaction to be employed in the reaction can be those described for the reaction of an N-acylamino acid or salt thereof.

While the molar ratio of the N-acylamino acid ester and the precursor polysaccharide or precursor modified polysaccharide employed in the reaction (N-acylamino acid ester: precursor polysaccharide or precursor modified polysaccharide) is not limited particularly as long as the reaction can be effected, it is preferably 50:1 to 20000:1. In view of an ability of providing a product having a stable emulsification performance without undergoing aggregation or segregation due to a salt, the ratio is preferably 100:1 to 20000:1, more preferably 200:1 to 20000:1, further preferably 300:1 to 20000:1, particularly 400:1 to 20000:1, and especially 500:1 to 20000:1. In view of an ability of providing a product capable of achieving satisfactory viscosity and water-dispersibility, the ratio is preferably 50:1 to 10000:1, more preferably 50:1 to 5000:1, further preferably 50:1 to 3000:1, particularly 50:1 to 2500:1.

The polysaccharide of the present invention can be separated from the reaction solution by using a known method such as crystallization, extraction, column purification, distillation and the like. It is also possible to use the reaction solution itself as a product. It is also possible to fractionate a preferred molecular weight range as appropriate for example by a gel permeation chromatography (GPC).

Emulsified Product.

The polysaccharide of the present invention is capable of resulting in a marked improvement in the emulsification stability of emulsified products, such as cosmetics, pharmaceuticals, agrochemicals, adhesives, resins, paints.

Especially by incorporating the polysaccharide of the present invention into a cosmetic product containing oily components and water, a satisfactory cosmetic emulsified product can be obtained.

The oily components employed in the cosmetic emulsified product according to the present invention may be a hydrocarbon oil such as liquid paraffin, squalane, isoparaffin, petrolatum and the like, an ester oil such as isopropyl myristate, isocetyl stearate, glycerin trioctanoate and the like, a silicone oil such as dimethylpolysiloxane, methylcyclopentasiloxane and the like, an oil-and-fat such as fatty acids, high molecular alcohols, olive oil, palm oil, safflower oil, castor oil, cottonseed oil and the like, waxes such as lanolin, carnauba wax and the like.

The cosmetic emulsified product of the present invention can be produced using an ordinary device fitted with a stirrer, a mixer, a dispersing machine and the like. For example, a method in which, in a part of water, the entire amount of the polysaccharide of the present invention is dissolved to form an aqueous solution which is combined with oily components followed by the remainder of the water, or a method in which, in a part of water, apart of the polysaccharide of the present invention is dissolved to form an aqueous solution which is combined with oily components followed by the remainder of the water containing the remainder of the polysaccharide of the present invention can be exemplified.

Into the cosmetic emulsified product of the present invention, the polysaccharide of the present invention is incorporated in an amount preferably of 0.001% by weight to 5% by weight. In view of further enhancement of the emulsion stabilizing effect, the lower limit is preferably 0.005% by weight, more preferably 0.01% by weight, particularly 0.05% by weight, especially 0.1% by weight. In view of avoiding an increase in the viscosity as far as possible, the upper limit is preferably 3% by weight, more preferably 1% by weight.

The viscosity of the cosmetic emulsified product of the present invention is 10 to 2000 mPa·s. In order to keep the favorable stability, the lower limit is preferably 30 mPa·s, more preferably 50 mPa·s. In order to keep the rapid spreadability, the upper limit is preferably 1000 mPa·s, more preferably 500 mPa·s.

The cosmetic emulsified product of the present invention may be added with other emulsion stabilizers or thickening agents as long as the effect of the present invention is not affected adversely. The composition of the invention may also contain substrates, auxiliary agents, surfactants, additives, powders and the like.

The cosmetic emulsified product of the present invention is not limited particularly, and may be tonic waters, lotions, creams, milky lotions, cosmetic liquids, hair shampoos, hair rinses, hair conditioners, body shampoos, enamels, foundations, eyeliners, eyebrow pencils, mascaras, lipsticks, face powders, powders, packs, fragrances, colognes, face washing foams, cleansing foams, cleansing oils, cleansing gels, makeup removers, tooth pastes, shaving foams, soaps, aerosols, bath salts, hair tonics, sunscreens, and the like. An application especially to a composition having a low viscosiry and a flowability allow the effect to be exerted readily.

EXAMPLES

The present invention is further described in detail in the following Examples, however the present invention is not intended to limit the following examples. The respective measurement methods are illustrated below.

n in Formula (1).

The n in Formula (1) was calculated using 1H-NMR (DMSO-d6). The measurement of 1H-NMR was conducted using Bruker AVANCE400. Typically, the following equation was employed for calculation.

$n$=[Integrated value per proton derived from methyl group at end of $R$ in Formula (1)(=($a$))]/[Integrated value per proton derived from saccharide unit in polysaccharide residue (=($b$))]×[weight average molecular weight of polysaccharide(= ($c$))]/[molecular weight of saccharide unit in polysaccharide residue(=($d$))]

The (d) in the equation was calculated using the following equation.

($d$)=[Molecular weight of saccharide unit constituting polysaccharide residue(=($e$))]+($a$)÷($b$)×[(chemical formula weight of —CO—X—NH—R)(=$f$)-(chemical formula weight of single hydrogen atom)(=$g$)]

The two equations are summarized and the n is obtained finally according to the following equation.

$n$=(($a$)×($c$))/[($b$)×($e$)+($a$)×{($f$)-($g$)}]

Weight Average Molecular Weight and Degree of Dispersion.

The weight average molecular weight, and the degree of dispersion (weight average molecular weight/number average molecular weight) was determined by a gel permeation chromatography (GPC) measurement. The column was TSKgel-α4000 and TSKgel-α6000 manufactured by TOSHO CORPORATION and the measurement was conducted at 50° C. As a mobile phase solvent, a 50 mM lithium bromide (manufactured by Junsei Chemical Co., Ltd.) dissolved in dimethylsulfoxide (manufactured by Junsei Chemical Co., Ltd., for HPLC) was employed. Detection was conducted using RID-10A manufactured by Shimadzu Corporation. A dextran (manufactured by Aldrich Corporation, peak top molecular weight=401300, 123600, 43500) was employed as a molecular weight standard to obtain a calibration curve with which the molecular weight was determined by extrapolation. A number average molecular weight (Mn) is defined as Mn=Σ(Hi (the "i"th molecule's peak height))/Σ(Hi/Mi (the "i"th molecule's molecular weight)). Similarly a weight average molecular weight (Mw) is defined as Mw=Σ(MiDHi)/Σ(Hi). The molecular weight was calculated using an LCsolution GPC software produced by Shimadzu Corporation.

IR Measurement.

IRPrestige-21 manufactured by Shimadzu Corporation was employed.

Production Example 1

15.3 g of Nα-lauroyl-L-glutamic acid (manufactured by Ajinomoto Co., Inc. "Amisoft" LA-D), 19.9 g of 1-ethyl-3-(3-dimethylaminopropyl)carbodiimide hydrochloride (manufactured by Tokyo Chemical Industry Co., Ltd.), 0.67 g of N,N-4-dimethylaminopyridine (manufactured by Wako Pure Chemical Industries Ltd.) were dissolved in 250 g of dimethylsulfoxide (manufactured by Junsei Chemical Co., Ltd.) at 75° C. While stirring continuously, 30 g of a corn starch having a weight average molecular weight of 1,200,000 (manufactured by Wako Pure Chemical Industries Ltd. Starch, Corn) was added and dissolved, and then stirred for 5 hours. After completion of the reaction followed by cooling to room temperature, 250 ml of methyl alcohol was added, and then after stirring the white precipitate was recovered by filtration, washed with methyl alcohol, dried to obtain a polysaccharide.

n: 590, weight average molecular weight: 1,760,000, Degree of dispersion: 44.1

IR Measurement results (KBr, $cm^{-1}$): 3363, 2927, 1653, 1153, 1081, 1023, 936

Production Example 2

Using GPC, the polysaccharide in the molecular weight range from 1,230,000 to 12,500,000 was fractionated from the polysaccharide obtained in Production Example 1 and the eluent was distilled off to obtain the intended substance.

n: 2000, weight average molecular weight: 5,920,000, Degree of dispersion: 1.47

Production Example 3

Using GPC, the polysaccharide in the weight average molecular weight range from 1,690,000 to 9,090,000 was fractionated from the polysaccharide obtained in Production Example 1 and the eluent was distilled off to obtain the intended substance.

n: 1800, weight average molecular weight: 5,310,000, Degree of dispersion: 1.26

Production Example 4

Using GPC, the polysaccharide in the weight average molecular weight range from 2,770,000 to 7,740,000 was fractionated from the polysaccharide obtained in Production Example 1 and the eluent was distilled off to obtain the intended substance.

n: 1800, weight average molecular weight: 5,290,000, Degree of dispersion: 1.09

Production Example 5

Using GPC, the polysaccharide in the weight average molecular weight range from 4,600,000 to 5,620,000 was fractionated from the polysaccharide obtained in Production Example 1 and the eluent was distilled off to obtain the intended substance.

n: 1700, weight average molecular weight: 5,110,000, Degree of dispersion: 1.00

Production Example 6

Using GPC, the polysaccharide in the weight average molecular weight range from 1,110,000 to 5,570,000 was fractionated from the polysaccharide obtained in Production Example 1 and the eluent was distilled off to obtain the intended substance.

n: 1000, weight average molecular weight: 2,980,000, Degree of dispersion: 1.22

Production Example 7

Using GPC, the polysaccharide in the weight average molecular weight range from 820,000 to 3,610,000 was fractionated from the polysaccharide obtained in Production Example 1 and the eluent was distilled off to obtain the intended substance.

n: 680, weight average molecular weight: 1,970,000, Degree of dispersion: 1.20

Production Example 8

Using GPC, the polysaccharide in the weight average molecular weight range from 620,000 to 2,970,000 was fractionated from the polysaccharide obtained in Production Example 1 and the eluent was distilled off to obtain the intended substance.

n: 510, weight average molecular weight: 1,530,000, Degree of dispersion: 1.24

Production Example 9

Except for using 7.81 g of Nα-lauroyl-L-glutamic acid, 10.05 g of 1-ethyl-3-(3-dimethylaminopropyl)carbodiimide hydrochloride, and 0.35 g of N,N-4-dimethylaminopyridine, the reaction was conducted similarly to Production Example 1, and then GPC was used to fractionate the polysaccharide in the weight average molecular weight range of 750,000 to 3,550,000, and then the eluent was distilled off to obtain the intended substance.

n: 300, weight average molecular weight: 2,050,000, Degree of dispersion: 1.37

Production Example 10

Except for using 5.34 g of Nα-lauroyl-L-glutamic acid, 6.58 g of 1-ethyl-3-(3-dimethylaminopropyl)carbodiimide hydrochloride, and 0.27 g of N,N-4-dimethylaminopyridine, the reaction was conducted similarly to Production Example 1, and then GPC was used to fractionate the polysaccharide in the weight average molecular weight range of 640,000 to 3,400,000, and then the eluent was distilled off to obtain the intended substance.

n: 200, weight average molecular weight: 1,980,000, Degree of dispersion: 1.34

Production Example 11

Except for using 2.61 g of Nα-lauroyl-L-glutamic acid, 3.32 g of 1-ethyl-3-(3-dimethylaminopropyl)carbodiimide hydrochloride, and 0.12 g of N,N-4-dimethylaminopyridine, the reaction was conducted similarly to Production Example 1, and then GPC was used to fractionate the polysaccharide in the weight average molecular weight range of 600,000 to 3,630,000, and then the eluent was distilled off to obtain the intended substance.

n: 100, weight average molecular weight: 2,030,000, Degree of dispersion: 1.35

Production Example 12

Except for using 0.41 g of Nα-lauroyl-L-glutamic acid, 0.53 g of 1-ethyl-3-(3-dimethylaminopropyl)carbodiimide hydrochloride, and 0.02 g of N,N-4-dimethylaminopyridine, the reaction was conducted similarly to Production Example 1, and then GPC was used to fractionate the polysaccharide in the weight average molecular weight range of 1,470,000 to 11,150,000, and then the eluent was distilled off to obtain the intended substance.

n: 50, weight average molecular weight: 5,500,000, Degree of dispersion: 1.33

Comparative Production Example 1

Using GPC, the polysaccharide in the weight average molecular weight range from 400,000 to 800,000 was fractionated from the polysaccharide obtained in Production Example 1 and the eluent was distilled off to obtain the intended substance.

n: 190, weight average molecular weight: 570,000, Degree of dispersion: 1.04

Comparative Production Example 2

Using GPC, the polysaccharide in the weight average molecular weight range from 100,000 to 200,000 was fractionated from the polysaccharide obtained in Production Example 1 and the eluent was distilled off to obtain the intended substance.

n: 47, weight average molecular weight: 140,000, Degree of dispersion: 1.04

Comparative Production Example 3

Using GPC, the polysaccharide in the weight average molecular weight range from 30,000 to 50,000 was fractionated from the polysaccharide obtained in Production Example 1 and the eluent was distilled off to obtain the intended substance.

n: 13, weight average molecular weight: 39,000, Degree of dispersion: 1.02

Comparative Production Example 4

The weight average molecular weight range from 400,000 to 800,000 was fractionated by GPC from 300 g of a corn starch (manufactured by Wako Pure Chemical Co., Ltd., Starch Corn) having a weight average molecular weight of 1,200,000, and the eluent was removed to obtain the intended substance. The weight average molecular weight was 510,000.

Comparative Production Example 5

100 g of Nα-lauroyl-L-glutamic acid was heated with stirring for 5 hours at 60° C. in 200 g of acetic anhydride, and then cooled to room temperature with stirring to allow a crystal to precipitate. This crystal was washed with 1000 mL of hexane and dried to obtain 72.4 g of Nα-lauroyl-L-glutamic anhydride.

Comparative Production Example 6

30 g of the corn starch obtained in Comparative Production Example 4 was dispersed in 250 mL of an ion exchange water at 5° C. This dispersion was adjusted to a pH within 10 to 11 by using a 3% aqueous solution of sodium hydroxide with stirring, and also while keeping the reaction temperature at 5° C., 14.5 g of Nα-lauroyl-L-glutamic acid anhydride obtained in Comparative Production Example 5 was added with stirring over 2 hr thereby conducting the reaction. After stirring further for 30 minutes, 500 mL of methyl alcohol was added and then a 75% aqueous solution of sodium hydroxide was added until pH5.0, and the white precipitate was recovered by filtration, washed with methyl alcohol and then dried.

n: 0, weight average molecular weight: 490,000, Degree of dispersion: 1.42

Comparative Production Example 7

Except that the fractionation range was 100,000 to 200,000, the fractionation was conducted under the condition similar to Comparative Production Example 4. The weight average molecular weight of the resultant corn starch was 15,000.

Comparative Production Example 8

Except that the fractionation range was 30,000 to 50,000, the fractionation was conducted under the condition similar to Comparative Production Example 4. The weight average molecular weight of the resultant corn starch was 37,000.

Comparative Production Example 9

Except for using the corn starch obtained in Comparative Production Example 7 instead of the corn starch obtained in Comparative Production Example 4, the reaction was conducted under the condition similar to Comparative Production Example 6.

n: 0, weight average molecular weight: 150,000, Degree of dispersion: 1.03

Comparative Production Example 10

Except for using the corn starch obtained in Comparative Production Example 8 instead of the corn starch obtained in Comparative Production Example 4, the reaction was conducted under the condition similar to Comparative Production Example 6.

n: 0, weight average molecular weight, 36,000, Degree of dispersion: 1.03

While Comparative Production Examples 6, 9, 10 were the production methods described in Patent Literature 2, the n was significantly low and it was known that the polysaccharide of the present invention could not be obtained.

Comparative Production Example 11

Except that the reaction temperature was 70° C., the reaction was conducted under the condition similar to Comparative Production Example 6.

n: 1.6, weight average molecular weight: 500,000, Degree of dispersion: 1.51

Comparative Production Example 12

Except that the reaction temperature was 70° C., the reaction was conducted under the condition similar to Comparative Production Example 9.

n: 0.43, weight average molecular weight: 140,000, Degree of dispersion: 1.05

Comparative Production Example 13

Except that the reaction temperature was 70° C., the reaction was conducted under the condition similar to Comparative Production Example 10.

n: 0.11, weight average molecular weight: 35,000, Degree of dispersion: 1.04

Comparative Production Example 14

Except for using 0.52 g of Nα-lauroyl-L-glutamic acid, 0.67 g of 1-ethyl-3-(3-dimethylaminopropyl)carbodiimide hydrochloride, and 0.03 g of N,N-4-dimethylaminopyridine, the reaction was conducted similarly to Production Example 1, and then GPC was used to fractionate the polysaccharide in the weight average molecular weight range of 800,000 to 1,500,000, and then the eluent was distilled off to obtain the intended substance.

n: 20, weight average molecular weight: 1,000,000, Degree of dispersion: 1.47

Preparation of Emulsion.

According to the ratios shown in Tables 2 to 4, Components (a) were mixed at 80° C. with stirring to achieve uniform dissolution, to which Components (b) dissolved uniformly in a purified water were added in portions also at 80° C., emulsified and cooled to room temperature.

Thereafter, Components (c) were mixed while stirring manually to obtain each of the emulsions of Examples 7 to 12 and Comparatives 10 to 24.

Each amount indicated in Tables 2 to 4 was in % by weight.

Components (a) employed are as follows.

Sorbitan monostearate: NIKKOL SS-10V manufactured by Nikko Chemicals Co., Ltd.

POE(20) sorbitan monostearate: NIKKOL TS-10V manufactured by Nikko Chemicals Co., Ltd.

Liquid paraffin: MORESCO WHITE P-55 manufactured by MORESCO Corporation

Evaluation.

Water-Dispersibility.

The dispersibility in water (water-dispersibility) was evaluated to show an easy incorporation. Each 0.3 g of a polysaccharide of the present invention and Comparative compound were mixed with 30 ml of water, stirred at 70° C., then transferred to a 50 ml volumetric cylinder, which was allowed to stand at room temperature for 1 hours, and then examined visually for the condition of the aqueous solution. At this time, the compound having a poor water-dispersibility should result in separation into an opaque layer and a transparent layer. This separation degree was observed and the mark of the volumetric cylinder was read and evaluated in accordance with the following criteria.

A: Almost no transparent layer is observed.
B: The volume of the transparent layer is under 5%.
C: The volume of the transparent layer is 5% or more and under 30%.
D: The volume of the transparent layer is 30% or more.

Viscosity.

80 ml of the emulsion was placed in a 100-ml beaker whose inner diameter was 50 mm, and the viscosity was measured using a DVL-B manufactured by Tokyo Keiki Inc., with a No. 4 spindle.

Aggregation or Segregation Due to Salts.

An emulsion containing 2.00% by weight of sodium chloride as Component (c) was prepared, and examined visually for the presence or the absence of segregation, and evaluated in accordance with the following criteria.

Not observed: No segregation is observed.
Slightly observed: Segregation is slightly observed.
Observed: Segregation is observed.

Spreadability.

The spreadability onto the skin of each emulsion was evaluated by 5 panelists (healthy adults). When a cosmetic material is applied onto the skin, a skid resistance reflecting the rheological characteristics such as the viscosity of the cosmetic material is experienced at an initial period of the application. When the cosmetic material is applied over a wider region as a thinner film, the resistance against the application is changed, and finally becomes a skid resistance similar to that upon a direct contact between skins as before the application of the cosmetic material. This phenomenon is called as "spreadability" here.

A: The number of panelists who felt that the spreadability is rapid when compared with Comparative Example 10 is 4 to 5.
B: The number of panelists who felt that the spreadability is rapid when compared with Comparative Example 10 is 3.
C: The number of panelists who felt that the spreadability is rapid when compared with Comparative Example 10 is 1 to 2.
D: The number of panelists who felt that the spreadability is rapid when compared with Comparative Example 10 is 0.

Low temperature stability evaluation.

Each emulsion was stored at 5° C., and the presence or absence of the segregation was inspected visually over time and evaluated according to the following criteria.

A: Segregation does not occur over 20 days or longer.
B: Segregation occurs on the 15th day or later but before 20th day.
C: Segregation occurs on the 10th day or later but before 15th day.
D: Segregation occurs before 10 days.

TABLE 1

| | Test Compound | n | Weight average molecular weight [$10^4$] | Degree of dispersion | Water-dispersibility |
|---|---|---|---|---|---|
| Ex. 1 | Product of Production Ex. 1 | 590 | 176 | 44.1 | A |
| Ex. 2 | Product of Production Ex. 2 | 2000 | 592 | 1.47 | A |
| Ex. 3 | Product of Production Ex. 3 | 1800 | 531 | 1.26 | A |
| Ex. 4 | Product of Production Ex. 4 | 1800 | 529 | 1.09 | B |
| Ex. 5 | Product of Production Ex. 5 | 1700 | 511 | 1.00 | B |
| Ex. 6 | Product of Production Ex. 6 | 1000 | 298 | 1.22 | A |
| Ex. 7 | Product of Production Ex. 7 | 680 | 197 | 1.20 | A |
| Ex. 8 | Product of Production Ex. 8 | 510 | 153 | 1.24 | A |
| Ex. 9 | Product of Production Ex. 9 | 300 | 205 | 1.37 | A |
| Ex. 10 | Product of Production Ex. 10 | 200 | 198 | 1.34 | A |
| Ex. 11 | Product of Production Ex. 11 | 100 | 203 | 1.35 | A |
| Ex. 12 | Product of Production Ex. 12 | 50 | 550 | 1.33 | B |
| Comp. Ex. 1 | Corn starch (Wako Pure Chemical Industries Ltd. | 0 | 120 | — | D |
| Comp. Ex. 2 | Hydroxypropyl starch phosphate (AkzoNobel, STRUCTURE XL) | 0 | — | — | D |
| Comp. Ex. 3 | Modified corn starch (AkzoNobel, AMEZ) | 0 | — | — | D |
| Comp. Ex. 4 | Product of Com. Production Example 6 | 0 | 49 | 1.42 | D |

TABLE 1-continued

|  | Test Compound | n | Weight average molecular weight [$10^4$] | Degree of dispersion | Water-dispersibility |
|---|---|---|---|---|---|
| Comp. Ex. 5 | Product of Com. Production Example 9 | 0 | 15 | 1.03 | D |
| Comp. Ex. 6 | Product of Com. Production Example 10 | 0 | 3.6 | 1.03 | D |
| Comp. Ex. 7 | Product of Com. Production Example 11 | 1.6 | 50 | 1.51 | D |
| Comp. Ex. 8 | Product of Com. Production Example 12 | 0.43 | 14 | 1.05 | D |
| Comp. Ex. 9 | Product of Com. Production Example 13 | 0.11 | 3.5 | 1.04 | D |
| Comp. Ex. 10 | Product of Com. Production Example 14 | 20 | 100 | 1.47 | D |

From Table 1, each polysaccharide of the present invention (Example 1 to 12) was proven to have a satisfactory water-dispersibility and be capable of being incorporated easily into a formulation. Each of Comparative Examples 1 to 9 whose n value was 0 or markedly low had a poor water-dispersibility. Even when the n was 20 and the weight average molecular weight was 1,000,000 (Comparative Example 10), the water-dispersibility was poor.

Among Examples, each of Examples 1 to 11 whose n values exceeded 50 had a water-dispersibility which was superior to that of Example 12 whose n value was 50. Also each of Examples whose degrees of dispersion was 1.10 or higher had a water-dispersibility which was superior to that of Example 4 whose degrees of dispersion was 1.09 or Example 5 whose degrees of dispersion was 1.00.

It was proven that Example 13 employing the polysaccharide of the present invention served to stabilize the emulsion when compared with Comparative Example 11 employing no polysaccharide. Comparative Examples 13 and 15 employing xanthane gum and hydroxypropyl starch phosphate exhibited poor rapidnesses of the spreadability. It was also proven that the use of the xanthane gum leaded to a great change in the viscosity and an alteration in the touch. Comparative Examples 14 and 16 employing a corn starch and a modified corn starch exhibited poor low temperature stabilities. Comparative Examples 12 employing Carbomer exhibited aggregation or segregation due to salts.

TABLE 2

|  |  | Ex. 13 | Comp. Ex. 11 | Comp. Ex. 12 | Comp. Ex. 13 | Comp. Ex. 14 | Comp. Ex. 15 | Comp. Ex. 16 |
|---|---|---|---|---|---|---|---|---|
| Component (a) | Sorbitan monostearate | 1.15 | 1.15 | 1.15 | 1.15 | 1.15 | 1.15 | 1.15 |
|  | POE(20) sorbitan monostearate | 1.25 | 1.25 | 1.25 | 1.25 | 1.25 | 1.25 | 1.25 |
|  | Liquid paraffin | 12.6 | 12.6 | 12.6 | 12.6 | 12.6 | 12.6 | 12.6 |
| Component (b) | Product of Production Ex. 1 | 0.50 |  |  |  |  |  |  |
|  | Carbomer (Carbopol 981, Noveon) |  |  | 0.50 |  |  |  |  |
|  | Xanthane gum (Sansho Co., Ltd., KELTROL CG-T) |  |  |  | 0.50 |  |  |  |
|  | Corn starch (Wako) |  |  |  |  | 0.50 |  |  |
|  | Hydroxypropyl starch phosphate (AkzoNobel, STRUCTURE XL) |  |  |  |  |  | 0.50 |  |
|  | Modified corn starch (AkzoNobel, AMAZE) |  |  |  |  |  |  | 0.50 |
|  | Methyl paraben | 0.36 | 0.36 | 0.36 | 0.36 | 0.36 | 0.36 | 0.36 |
|  | Purified water | Remainder | Remainder | Remainder | Remainder | Remainder | Remainder | Remainder |
| Component (c) | Sodium chloride | 2.00 | 2.00 | 2.00 | 2.00 | 2.00 | 2.00 | 2.00 |
|  | Purified water | 8.00 | 8.00 | 8.00 | 8.00 | 8.00 | 8.00 | 8.00 |
| TOTAL |  | 100 | 100 | 100 | 100 | 100 | 100 | 100 |
| Evaluation | Viscosity (mPa·s) | 107 | 53 | — | 2051 | 65 | 79 | 84 |
|  | Aggregation or segregation due to salts | Not observed | Not observed | Observed | Not observed | Not observed | Not observed | Not observed |
|  | Spreadability | A | — | — | D | C | D | C |
|  | Low temperature stability (5° C.) | A | D | — | A | D | B | D |

TABLE 3

| | | Ex. 14 | Ex. 15 | Ex. 16 | Ex. 17 | Comp. Ex. 17 | Comp. Ex. 18 | Comp. Ex. 19 |
|---|---|---|---|---|---|---|---|---|
| Component (a) | Sorbitan monostearate | 1.15 | 1.15 | 1.15 | 1.15 | 1.15 | 1.15 | 1.15 |
| | POE(20) sorbitan monostearate | 1.25 | 1.25 | 1.25 | 1.25 | 1.25 | 1.25 | 1.25 |
| | Liquid paraffin | 12.60 | 12.60 | 12.60 | 12.60 | 12.60 | 12.60 | 12.60 |
| Component (b) | Product of Production Ex. 2 (degree of dispersion: 1.47, AMW: 592 × 10$^4$) | 0.50 | | | | | | |
| | Product of Production Ex. 3 (degree of dispersion: 1.26) | | 0.50 | | | | | |
| | Product of Production Ex. 4 (degree of dispersion: 1.09) | | | 0.50 | | | | |
| | Product of Production Ex. 5 (degree of dispersion: 1.00) | | | | 0.50 | | | |
| | Product of Comparative Production Ex. 1 (AMW: 57 × 10$^4$) | | | | | 0.50 | | |
| | Product of Comparative Production Ex. 2 (AMW: 14 × 10$^4$) | | | | | | 0.50 | |
| | Product of Comparative Production Ex. 3 (AMW: 3.9 × 10$^4$) | | | | | | | 0.50 |
| | Methyl paraben | 0.36 | 0.36 | 0.36 | 0.36 | 0.36 | 0.36 | 0.36 |
| | Purified water | Remainder | Remainder | Remainder | Remainder | Remainder | Remainder | Remainder |
| Component (c) | Sodium chloride | 2.00 | 2.00 | 2.00 | 2.00 | 2.00 | 2.00 | 2.00 |
| | Purified water | 8.00 | 8.00 | 8.00 | 8.00 | 8.00 | 8.00 | 8.00 |
| TOTAL | | 100.00 | 100.00 | 100.00 | 100.00 | 100.00 | 100.00 | 100.00 |
| Evaluation | Viscosity (mPa · s) | 113 | 101 | 97 | 106 | 100 | 111 | 98 |
| | Aggregation or segregation due to salts | Not observed | Not observed | Not observed | Not observed | Slightly observed | observed | observed |
| | Spreadability | A | A | C | C | C | C | C |
| | Low temperature stability (5° C.) | A | A | B | B | D | D | D |

As evident from Table 3, the emulsions of Comparative Examples 17 to 19 employing the polysaccharide whose weight average molecular weights were less than 1,100,000, exhibited poor low temperature stabilities. The aggregation or segregation due to salts was observed especially in Comparative Examples 18 and 19 employing the polysaccharide whose weight average molecular weights were low.

Among Examples, Examples 13 to 15 employing the polysaccharide whose degrees of dispersion were 1.10 or higher exhibited an excellence in the rapid spreadability and the low temperature stability when compared with Examples 16 and 17 employing the polysaccharide whose degrees of dispersion were 1.09, 1.00.

TABLE 4

| | | Comp. Ex. 20 | Comp. Ex. 21 | Comp. Ex. 22 | Comp. Ex. 23 | Comp. Ex. 24 | Comp. Ex. 25 | Comp. Ex. 26 |
|---|---|---|---|---|---|---|---|---|
| Component (a) | Sorbitan monostearate | 1.15 | 1.15 | 1.15 | 1.15 | 1.15 | 1.15 | 1.15 |
| | POE(20) sorbitan monostearate | 1.25 | 1.25 | 1.25 | 1.25 | 1.25 | 1.25 | 1.25 |
| | Liquid paraffin | 12.60 | 12.60 | 12.60 | 12.60 | 12.60 | 12.60 | 12.60 |
| Component (b) | Product of Comp. Production Ex. 6 | 0.50 | | | | | | |
| | Product of Comp. Production Ex. 9 | | 0.50 | | | | | |

TABLE 4-continued

|  |  | Comp. Ex. 20 | Comp. Ex. 21 | Comp. Ex. 22 | Comp. Ex. 23 | Comp. Ex. 24 | Comp. Ex. 25 | Comp. Ex. 26 |
|---|---|---|---|---|---|---|---|---|
|  | Product of Comp. Production Ex. 10 |  |  | 0.50 |  |  |  |  |
|  | Product of Comp. Production Ex. 11 |  |  |  | 0.50 |  |  |  |
|  | Product of Comp. Production Ex. 12 |  |  |  |  | 0.50 |  |  |
|  | Product of Comp. Production Ex. 13 |  |  |  |  |  | 0.50 |  |
|  | Product of Comp. Production Ex. 14 |  |  |  |  |  |  | 0.50 |
|  | Methyl paraben | 0.36 | 0.36 | 0.36 | 0.36 | 0.36 | 0.36 | 0.36 |
|  | Purified water | Remainder | Remainder | Remainder | Remainder | Remainder | Remainder | Remainder |
| Component (c) | Sodium chloride | 2.00 | 2.00 | 2.00 | 2.00 | 2.00 | 2.00 | 2.00 |
|  | Purified water | 8.00 | 8.00 | 8.00 | 8.00 | 8.00 | 8.00 | 8.00 |
| TOTAL |  | 100.00 | 100.00 | 100.00 | 100.00 | 100.00 | 100.00 | 100.00 |
| Evaluation | Viscosity (mPa·s) | 100 | 99 | 97 | 105 | 102 | 100 | 104 |
|  | Aggregation or segregation due to salts | Slightly observed | observed | observed | Slightly observed | observed | observed | Slightly observed |
|  | Spreadability | C | C | C | C | C | C | C |
|  | Low temperature stability (5° C.) | D | D | D | D | D | D | D |

Comparative Examples 20 to 26 employing the polysaccharide, whose n values were 0 or markedly low, exhibited poor low temperature stabilities. Even with the polysaccharide of Comparative Production Example 14 having an n value of 20 and a weight average molecular weight of 1,000,000, the low temperature stability was poor.

Formulation Example 1

Milky Lotion

TABLE 5

| INCI Name | Parts |
|---|---|
| Liquid paraffin | 12.000 |
| Octyldodeceth-10 | 2.325 |
| Octyldodeceth-5 | 0.175 |
| Squalane | 0.050 |
| Di(octyldodecyl/phytosteryl/behenyl) lauroyl glutamate | 0.025 |
| Butylene glycol | 2.500 |
| Product of Production Example 1 | 0.250 |
| Dipotassium Glycyrrhizate | 0.050 |
| Methylparaben | 0.100 |
| Purified water | Remainder |
| TOTAL | 100.000 |

The milky lotion shown above was a sufficiently stable milky lotion.

It is significant that by means of a specific polysaccharide having an excellent water-dispersibility of the present invention, it becomes capable of providing emulsions, cosmetics, pharmaceuticals, agrochemicals, adhesives, resins and paints each of which exhibits a rapid spreadability onto the skin, does not undergo aggregation or segregation due to salts and shows an excellent low temperature stability.

The invention claimed is:

1. A polysaccharide represented by formula (1):

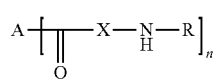

(1)

wherein:
A represents a polysaccharide residue;
R represents an acyl group derived from a saturated or unsaturated fatty acid having 8 to 12 carbon atoms;
—CO—X—NH— represents an amino acid residue selected from the group consisting of aspartic acid and glutamic acid;
n is an integer of 100 to 3,000; and
said polysaccharide has a weight average molecular weight of 1,500,000 to 8,000,000,
wherein A represents one or more selected from the group consisting of a cellulose residue, a starch residue, a hydroxyethylcellulose residue, a methylcellulose residue, an ethylcellulose residue, and a hydroxypropylcellulose residue, and
wherein said polysaccharide has a degree of dispersion of 1.5 to 50.

2. A polysaccharide according to claim 1, wherein said amino acid is glumatic acid.

3. An emulsified product, comprising a polysaccharide represented by formula (1):

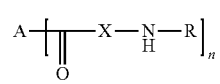

(1)

wherein:
A represents a polysaccharide residue;
R represents an acyl group derived from a saturated or unsaturated fatty acid having 8 to 12 carbon atoms;
—CO—X—NH- represents an amino acid residue selected from the group consisting of aspartic acid and glutamic acid;

n is an integer of 100 to 3,000; and said polysaccharide has a weight average molecular weight of 1,500,000 to 8,000,000, wherein A represents one or more selected from the group consisting of a cellulose residue, a starch residue, a hydroxyethylcellulose residue, a methylcellulose residue, an ethylcellulose residue, and a hydroxypropylcellulose residue, and wherein said polysaccharide has a degree of dispersion of 1.5 to 50.

4. An emulsified product, comprising a polysaccharide represented by formula (1):

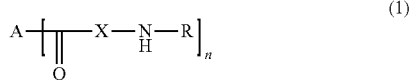

wherein:

A represents a polysaccharide residue;

R represents an acyl group derived from a saturated or unsaturated fatty acid having 8 to 12 carbon atoms;

—CO—X—NH- represents an amino acid residue selected from the group consisting of aspartic acid and glutamic acid;

n is an integer of 100 to 3,000; and said polysaccharide has a weight average molecular weight of 1,500,000 to 8,000,000, wherein A represents one or more selected from the group consisting of a cellulose residue, a starch residue, a hydroxyethylcellulose residue, a methylcellulose residue, an ethylcellulose residue, and a hydroxypropylcellulose residue, wherein said polysaccharide has a degree of dispersion of 1.5 to 50, and wherein said polysaccharide is present in an amount of 0.001% by weight to 5% by weight, based on the total weight of said emulsified product.

5. An emulsified product, which comprises:

(a) a polysaccharide represented by formula (1):

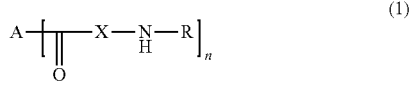

wherein:

A represents a polysaccharide residue;

R represents an acyl group derived from a saturated or unsaturated fatty acid having 8 to 12 carbon atoms;

—CO—X—NH- represents an amino acid residue selected from the group consisting of aspartic acid and glutamic acid;

n is an integer of 100 to 3,000; and said polysaccharide has a weight average molecular weight of 1,500,000 to 8,000,000, wherein A represents one or more selected from the group consisting of a cellulose residue, a starch residue, a hydroxyethylcellulose residue, a methylcellulose residue, an ethylcellulose residue, and a hydroxypropylcellulose residue, and wherein said polysaccharide has a degree of dispersion of 1.5 to 50; and (b) an oily component and water.

6. A method for producing a polysaccharide according to claim 1, said method comprising reacting an N-acylamino acid, salt thereof, anhydride thereof, or ester thereof with a precursor polysaccharide or a precursor modified polysaccharide.

7. The polysaccharide according to claim 1, wherein said amino acid is aspartic acid.

8. The emulsified product according to claim 3, wherein said amino acid is aspartic acid.

9. The emulsified product according to claim 3, wherein said amino acid is glutamic acid.

10. The emulsified product according to claim 4, wherein said amino acid is aspartic acid.

11. The emulsified product according to claim 4, wherein said amino acid is glutamic acid.

12. The emulsified product according to claim 5, wherein said amino acid is aspartic acid.

13. The emulsified product according to claim 5, wherein said amino acid is glutamic acid.

* * * * *